United States Patent
Zegarelli et al.

(12)

(10) Patent No.: US 6,523,179 B1
(45) Date of Patent: *Feb. 25, 2003

(54) DISPOSABLE PATIENT FACE MASK

(76) Inventors: Peter J. Zegarelli, 11 Raafenberg Rd., Pocantico Hills, NY (US) 10591; Mitchell Steinberg, 85 Coves Run, Oyster Bay Cove, NY (US) 11791

( * ) Notice: Subject to any disclaimer, the term of this patent is extended or adjusted under 35 U.S.C. 154(b) by 0 days.

This patent is subject to a terminal disclaimer.

(21) Appl. No.: 09/929,541

(22) Filed: Aug. 13, 2001

(51) Int. Cl.7 ................................................ A42B 1/00
(52) U.S. Cl. .............................. 2/9; 2/206; 128/206.19; 128/206.21; 128/857
(58) Field of Search ..................... 2/9, 206; 128/857, 128/206.21, 206.19, 859, 206.24, 206.25, 206.28; 433/215, 229

(56) References Cited

U.S. PATENT DOCUMENTS

| | | | | | |
|---|---|---|---|---|---|
| 4,737,104 A | * | 4/1988 | Croll | .......................... | 433/141 |
| 5,303,423 A | * | 4/1994 | Gazzara et al. | ..................... | 2/9 |
| 5,424,787 A | * | 6/1995 | Zegarelli | ..................... | 351/111 |
| 5,694,925 A | * | 12/1997 | Reese et al. | ........... | 128/206.19 |
| 5,927,280 A | * | 7/1999 | Miyake | ...................... | 128/857 |
| 6,079,980 A | * | 6/2000 | Durand | ....................... | 433/137 |
| 6,185,740 B1 | * | 2/2001 | Zegarelli et al. | ..................... | 2/9 |

* cited by examiner

*Primary Examiner*—John J. Calvert
*Assistant Examiner*—Katherine Moran

(57) ABSTRACT

A tissue face mask similar to that used by a dentist but placed in covering relation over the face of a patient preparatory to a dental procedure using a laser or similar light-emitting device in which mask there are shaping stays that are manually conformed to the facial features of the patient to prevent harm to the patient from the emitted light of the dental procedure.

1 Claim, 1 Drawing Sheet

DISPOSABLE PATIENT FACE MASK

The present invention relates generally to protective face masks, and more particularly to face masks primarily for dentistry practice.

EXAMPLES OF THE PRIOR ART

In U.S. Pat. No. 5,303,423 for Face Shield/Mask Combination issued to Gazzara et al. on Apr. 19, 1994, there is provided for use during medical procedures for the protection of medical personnel who, during such procedures, are subject to blood and other bodily fluids coming into contact with their face, a suitable face mask to obviate such contact, it being explained that such contact is dangerous because of the potential presence of the deadly AIDS virus or other harmful pathogens.

Thus, in dentistry practice, a face mask is used to obviate disease transmission between a patient and dentist, and the dentist, the user of the face mask, will dispose of the face mask between dental procedures to obviate disease transmission between patients. To facilitate the use of the face mask, used without exception by the dentist, the elimination of the discomfort of the elastic ear loops is the thrust of U.S. Pat. No. 5,424,787 for Eyeglasses With Mask Support Attachment Means issued to Peter J. Zegarelli, a co-inventor of the present invention, on Jun. 13, 1995, and exemplifies the prior art effort concerned with the face mask for the dentist's use.

Underlying the present invention is the recognition that often the dental procedure provided the patient will entail the use of light-emitting devices, including lasers, as exemplified by the commercially available EXcimer laser, dental light cure bonding lights, and dental bleaching lights, in the use of which the administering dentist uses for his/her protection against eye damage eye wear, including goggles and eyeglasses, equipped with light filters, which are typically an applied coating of a range of colors, e.g., purple, green, orange, yellow, light blue, grey, brown, and pink, on glass. The filters absorb the frequency of light in accordance with the colors thereof and in so doing contribute to preventing light impingement on the eyes of the dentist behind the filters.

In a contemplated end use, an EXcimer laser, or equivalent laser, is now in popular use for soft tissue surgery in dental procedures and during such use a dentist prudently uses goggles with light-absorbing filters to obviate eye damage. Heretofore, such protection was provided only to the dentist and the patient, although in the environment of and thus similarly subjected to the harmful effects to his/her eye sight by ambient emitted high intensity light was without protection.

Broadly, it is an object of the present invention to provide a face mask affording protection to the patient, thus addressing a shortcoming of the prior art.

More particularly, it is an object to provide a dental patient's face mask affording effective protection against emitted light in close proximity to the patient.

The description of the invention which follows, together with the accompanying drawings should not be construed as limiting the invention to the example shown and described, because those skilled in the art to which this invention appertains will be able to devise other forms thereof within the ambit of the appended claims.

Figure 3:
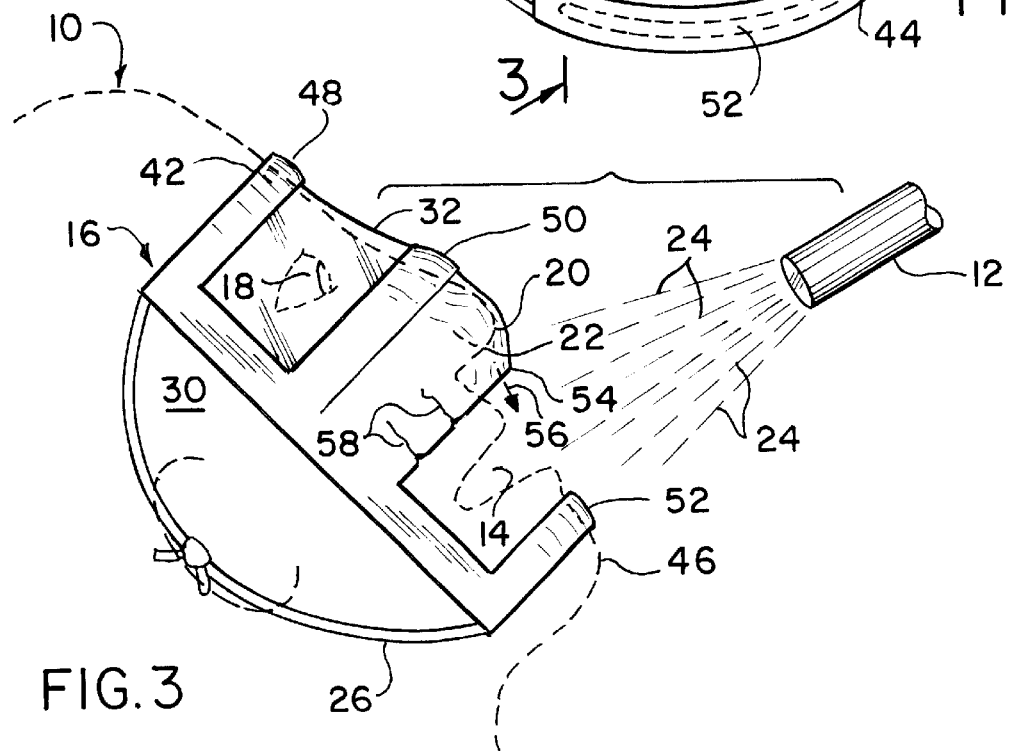
FIG. 3 is side elevational view of the face mask in use over a patient's face and in section taken along line 3—3 of FIG. 2.

Part of the preparation of a patient 10 for protection against harmful consequences of doing soft tissue surgery using a laser, or involving a similar high intensity light source, noted at 12, the target site of the light being a patient's mouth 14 from the source 12 from a clearance position above the patient, as illustrated in FIG. 3, is the prone, or nearly prone, positioning of the patient 10 in a chair head support and thus in an upwardly facing relation. Unlike the dentist's face mask, the patient's face mask 16 is horizontally, rather than vertically, oriented in covering relation over the area to be protected, namely, the eyes 18 and nose 20 and nostrils 22 surrounding area, through which surrounding area in practice patients report an inadvertent "look down" phenomenon sighting the emitted light 24. The positioning elastic loops 26 and 28 are used, but are not as essential as in the use of the dentist's face mask.

Because the light source 12 and the rays 24 emitted are above and in facing relation to the patient 10 as illustrated, for an interposed protecting position between the source 12 and patient 10 the face mask 16 requires being imparted with a shape conforming as closely as possible to the shapes of the facial features of each patient 10 fitted with the face mask 16. To this end, face mask 16 is construction wise similar in many respects to a typical dentist's face mask, such as having its stock dimensions of 6¾ inches by 3½ inches, the former dimension possibly being increased to 8 inches in order to adequately cover the eyes 18 and extend to the patient's temple area 30, and also being sized for both adult and pedo usage.

In addition however, and in accordance with the present invention, the patient's face mask 16 has as constituent components an upper light filter of known construction and known light frequency-absorbing utility designated 32 and in the specific form of a plastic panel 32, of a preferred minimal size of 1 inch by 6 inches, an appropriately attached depending tissue portion 34, of the same tissue construction material used in a dentist's face mask, and at least two horizontally oriented spaced apart shape-conforming stays 36 and 38 each of malleable metal construction material and each adhesively or otherwise appropriately contained within a stay-enclosing pocket or compartment 40. Stay 36 above the see-through panel 32, which panel 32 is coincident with the location of the patient's eyes 18, is coincident with the patient's forehead 42, and stay 38 below the panel 32 coincident with the location of the bridge of the patient's nose 20. In the embodiment selected for illustration, the face mask 16 includes an embodied third stay 44 coincident with the location of the patient's chin 46.

Figure 1:
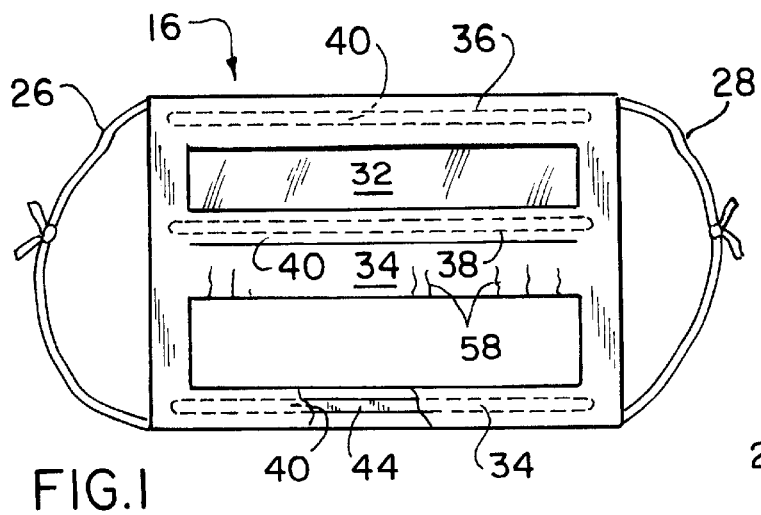
FIG. 1 is a front elevational view of a dental face mask used for patient protection in accordance with the present invention.
Figure 2:
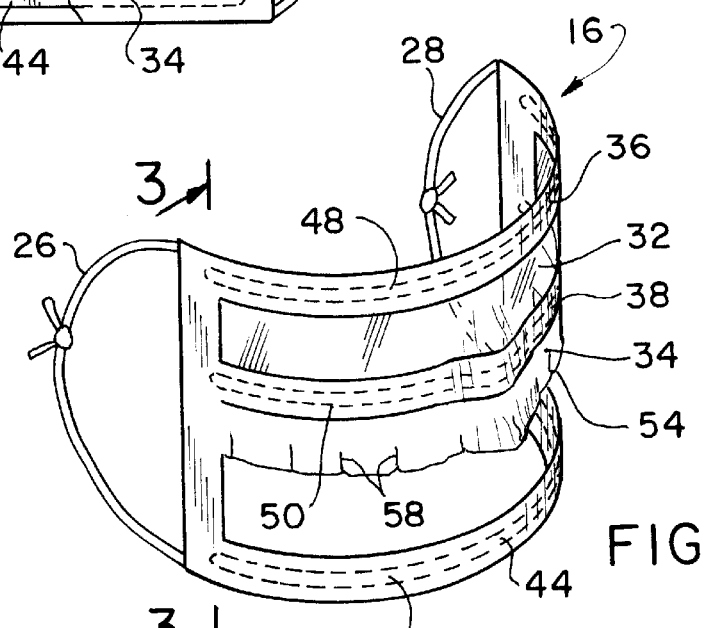
FIG. 2 is an isolated perspective view of the face mask illustrating the typical shape configurations of the stay constituents thereof contributing to the fit of the face mask.

After placement of the face mask 16 in covering relation over the patient's face, the dentist or a dental assistant will manually shape the top stay 36 to the shape of the patient's forehead 42 and in a curvilinear configuration extending from one side temple 30 to the other, followed next by shaping stay 38 to a substantially inverted U-shape, a shape typical of a bridge of a nose, to the patient's nose, and lastly shaping stay 44 to the curvilinear shape of the patient's chin 46. The assumed noted shapes of the top, middle and bottom stays 36, 38 and 44 are respectively depicted at 48, 50 and 52 in FIG. 2, and in practice have been found to contribute to a good conforming fit of the face mask 16 to the unique facial shape of the patient 10, effective against the occurrence of the previously noted "look down" phenomenon or other light transmission 24 of light source 12 from bypassing the facial mask 16 in its advantageous interposed position between the source 12 and the prone patient 10.

In some instances, the bottom edge 54 of the tissue portion 34 will be pulled down, a degree of movement 56 allowed by the pleat construction 58 of the tissue portion 34 so that the bottom edge 54 serves as an effective closure for the mask 16.

While the face mask for practicing the within inventive method, as well as said method herein shown and disclosed in detail is fully capable of attaining the objects and providing the advantages hereinbefore stated, it is to be understood that it is merely illustrative of the presently preferred embodiment of the invention and that no limitations are intended to the detail of construction or design herein shown other than as defined in the appended claims.

What is claimed is:

1. For patient preparation to provide protection against light emissions from a selected one of a laser, a bonding light and a bleaching light used in a dental procedure, an improved method of obviating a harmful consequence thereof comprising the steps of:

(1) positioning prone on a support a patient facing upwardly in relation to a potential source of light transmissions;

(2) using a face mask constituent with an upper color plastic light filter, a depending tissue lower portion, and at least two horizontally oriented spaced apart shape-conforming stays of malleable metal construction material on opposite sides of said plastic light filter;

(3) placing said aforesaid constituent face mask in covering relation over said patient's face with said plastic light filter coincident with the eyes of said patient and said tissue portion over said patient's nose; and (4) manually shaping each said shape-conforming stay respectively to the underlying shapes of the forehead and nose of said patient;

whereby harm is obviated by said interposed position of said face mask between said prone patient and said source of said light transmissions.

* * * * *